United States Patent
Kludt et al.

(10) Patent No.: US 9,579,499 B2
(45) Date of Patent: Feb. 28, 2017

(54) SOUND PROCESSING USING A MASKING MODEL

(71) Applicant: Cochlear Limited, Macquarie University (AU)

(72) Inventors: Eugen Kludt, Macquarie University (AU); Andreas Büchner, Macquarie University (AU)

(73) Assignee: Cochlear Limited, Macquarie University, NSW (AU)

( * ) Notice: Subject to any disclaimer, the term of this patent is extended or adjusted under 35 U.S.C. 154(b) by 897 days.

(21) Appl. No.: 13/668,348

(22) Filed: Nov. 5, 2012

(65) Prior Publication Data
US 2014/0079226 A1 Mar. 20, 2014

Related U.S. Application Data

(60) Provisional application No. 61/702,229, filed on Sep. 17, 2012.

(51) Int. Cl.
*H04R 25/00* (2006.01)
*A61N 1/05* (2006.01)
*A61N 1/36* (2006.01)

(52) U.S. Cl.
CPC ....... *A61N 1/0541* (2013.01); *A61N 1/36032* (2013.01); *H04R 25/356* (2013.01); *H04R 25/606* (2013.01); *H04R 25/75* (2013.01)

(58) Field of Classification Search
CPC ...... H04R 25/75; H04R 25/35; H04R 25/353; H04R 25/356; H04R 25/606; H04R 2225/43; H04R 2460/03; G10L 19/025; G10L 25/18; A61N 1/0541; A61N 1/36032
See application file for complete search history.

(56) References Cited

U.S. PATENT DOCUMENTS

| 7,272,446 | B2 | 9/2007 | Parker et al. | |
| 8,005,246 | B2 * | 8/2011 | Ribic | 381/316 |
| 2009/0177247 | A1 | 7/2009 | Neal et al. | |
| 2011/0249843 | A1 * | 10/2011 | Holmberg | H04R 25/353 381/316 |

OTHER PUBLICATIONS

Waldo Nogueira et al.; A Psychoacoustic 'NofM'-Type Speech Coding Strategy for Cochlear Implants; Journal on Applied Signal Processing, vol. 127, Nr. 18, pp. 3044-3059; Nov. 2005.
Nucleus Technical Reference Manual, Module 3: Programming Fundamentals; Cochlear Limited; Nov. 1999.

* cited by examiner

*Primary Examiner* — Duc Nguyen
*Assistant Examiner* — Kile Blair

(57) ABSTRACT

Methods, systems, and devices for determining a stimulus based on a masking model of human hearing are disclosed. An example method includes receiving a signal that includes information indicative of one or more spectral components of a sound. The example method also includes determining a masking curve that includes information indicative of one or more masking spectral components. The masking curve is determined according to a masking model of human hearing that accounts for at least an effect due to temporal masking. The example method further includes generating a stimulus based on a difference between the one or more spectral components and the one or more masking spectral components. The stimulation allows a recipient to perceive at least a portion of the sound.

28 Claims, 5 Drawing Sheets

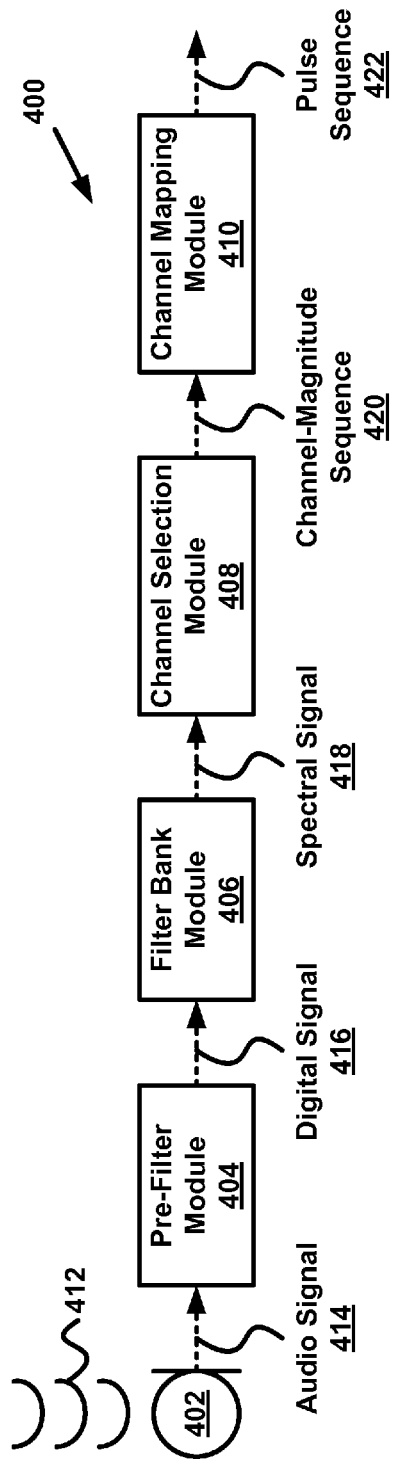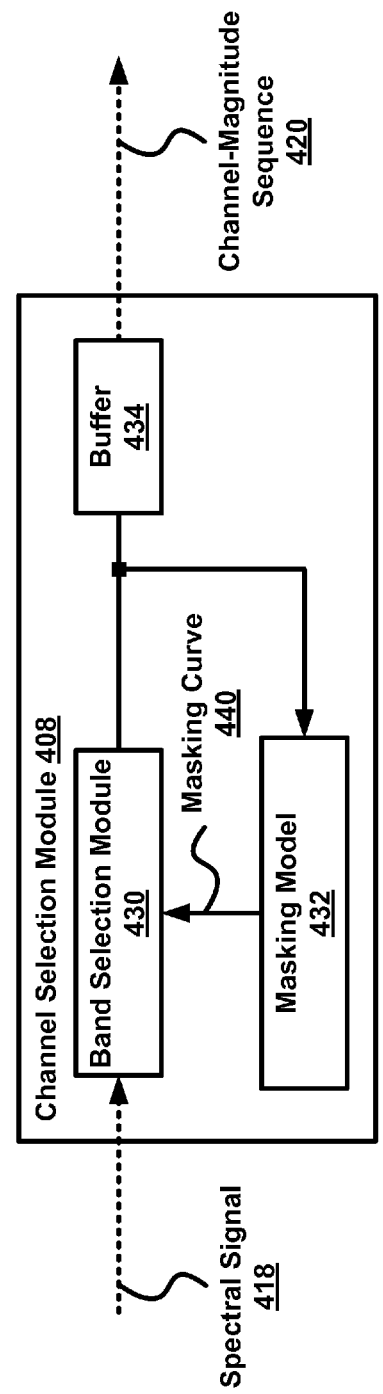
FIG. 4A
FIG. 4B

SOUND PROCESSING USING A MASKING MODEL

CROSS-REFERENCE TO RELATED APPLICATION

This application claims priority to U.S. Provisional Patent Application Ser. No. 61/702,229 filed Sep. 17, 2012, the contents of which are hereby incorporated by reference.

BACKGROUND

Individuals who suffer from certain types of hearing loss may benefit from the use of a hearing prosthesis. Depending on the type and the severity of the hearing loss, an individual can employ a hearing prosthesis to assist a recipient in perceiving at least a portion of a sound. A partially implantable hearing prosthesis typically includes an external component that performs at least some processing functions and an implanted component that at least delivers a stimulus to a body part in an auditory pathway, such as a cochlea, an auditory nerve, a brain, or any other body part that contributes to the perception of sound. In the case of a totally implantable hearing prosthesis, the entire device is implanted in the body of the recipient.

SUMMARY

A first method is provided. The first method includes receiving a signal that includes information indicative of one or more spectral components of a sound. The first method also includes determining a masking curve that includes information indicative of one or more masking spectral components. The masking curve is determined according to a masking model of human hearing that accounts for at least an effect due to temporal masking. The first method further includes generating a stimulus based on a difference between the signal and the masking curve. The stimulation allows a recipient to perceive at least a portion of the sound.

A second method is also provided. The second method includes determining M spectral components of a sample of an audio signal. M is an integer greater than one. The second method also includes selecting N spectral components to include in a stimulation signal from the M spectral components. N is an integer greater than zero and less than M, and the N spectral components depend on at least N previously selected spectral components. The second method further includes generating a stimulation signal based on the N spectral components. The stimulation signal includes information indicative of a stimulus that allows a recipient to perceive at least a portion of the audio signal A non-transitory computer-readable memory having stored thereon instructions executable by a computing device to perform functions is provided. The functions include determining an initial masking curve that includes one or more masking spectral components. The initial masking curve is based on a masking model of human hearing that accounts for at least a temporal masking effect. The functions also include generating a modified masking curve by applying a modification factor to the initial masking curve. The modified masking curve includes one or more modified masking spectral components. The functions further include determining one or more differences between one or more spectral components of an audio sample and the one or more modified masking spectral components. The audio sample includes information indicative of a sound. The functions additionally include identifying a maximum difference from the one or more differences and selecting a selected spectral component corresponding to the maximum difference. The functions further include generating a stimulus based on at least the selected spectral component. The stimulus causes a recipient to perceive at least a portion of the sound.

Additionally, a sound processor is also provided. The sound processor is configured to determine a digital sample of an audio signal. The sound processor is also configured to determine one or more spectral components of the digital sample. The sound processor is further configured to select a one or more of the spectral components to include in a stimulation signal. The one or more of the spectral components selected depends on one or more prior spectral components included in a prior stimulation signal. The sound processor is additionally configured to generate the stimulation signal. The stimulation signal includes information indicative of a stimulus that allows a recipient to perceive at least a portion of the audio signal.

These as well as other aspects and advantages will become apparent to those of ordinary skill in the art by reading the following detailed description, with reference where appropriate to the accompanying drawings. Further, it is understood that this summary is merely an example and is not intended to limit the scope of the invention as claimed.

BRIEF DESCRIPTION OF THE FIGURES

Presently preferred embodiments are described below in conjunction with the appended drawing figures, wherein like reference numerals refer to like elements in the various figures, and wherein:

FIG. 4A is a block diagram of a system for processing an audio signal, according to an example;

FIG. 4B is a block diagram of a channel mapping module depicted in FIG. 4A, according to an example;

DETAILED DESCRIPTION

The following detailed description describes various features, functions, and attributes of the disclosed systems, methods, and devices with reference to the accompanying figures. In the figures, similar symbols typically identify similar components, unless context dictates otherwise. The illustrative embodiments described herein are not meant to be limiting. It will be readily understood that the aspects of the present disclosure, as generally described herein, and illustrated in the figures, can be arranged, substituted, combined, separated, and designed in a wide variety of different configurations, all of which are contemplated herein.

1. Example Hearing Prosthesis

Figure 1:
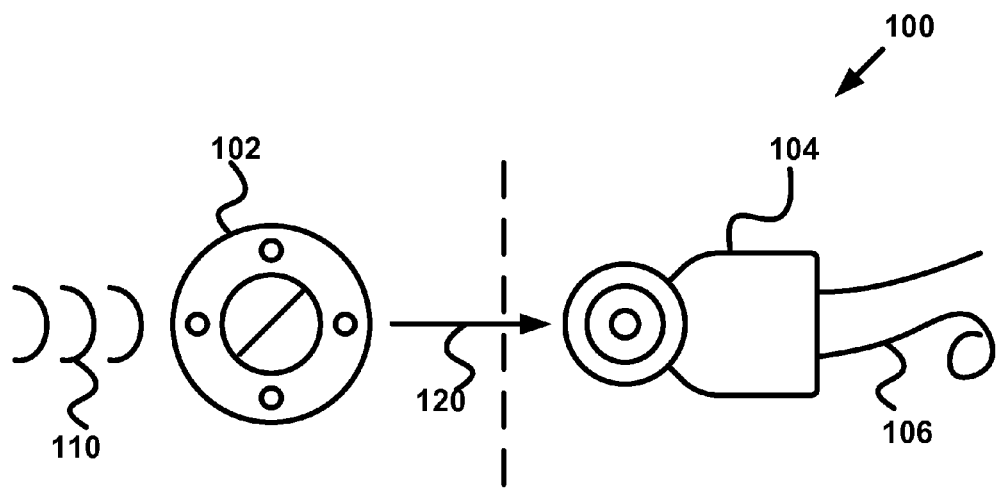
FIG. 1 illustrates components of a hearing prosthesis, according to an example.

FIG. 1 illustrates a hearing prosthesis 100. The hearing prosthesis 100 includes a processing unit 102 and an implanted unit 104. A recipient utilizes the hearing prosthesis 100 to assist the recipient in perceiving a sound. In FIG. 1, the hearing prosthesis 100 is a partially implantable cochlear implant. The processing unit 102 is external to the recipient's body, and the implanted unit 104 is implanted in the recipient's body. In another example, the hearing prosthesis 100 is a totally implantable hearing prosthesis, in which case the processing unit 102 and the implanted unit 104 are implanted in the recipient's body. Additionally, a single enclosure may contain the components of the processing unit 102 and the implanted unit 104. In yet another example, the hearing prosthesis 100 is an auditory brain stem implant or any other hearing prosthesis or combination of hearing prostheses now known (e.g., a hearing prosthesis system combining electrical and mechanical stimulation) or later developed.

The processing unit 102 receives a sound 110. In one example, the sound 110 originates from a source in an environment. In another example, the sound 110 originates from an external device configured to send the sound signal to the processing unit 102, such as an audio streaming device. The processing unit 102 processes the sound 110 and generates a stimulation signal based on the sound 110.

The processing unit 102 also provides a power signal to the implanted unit 104. The processing unit 102 modulates the power signal based on the stimulation signal such that a modulated power signal 120 contains both the power signal and the stimulation signal. In one example, the processing unit 102 inductively transfers the modulated power signal 120 to the implanted unit 104. In another example, the processing unit 102 transmits the modulated power signal 120 to the implanted unit 104 using a different transmission technique.

The implanted unit 104 receives the modulated power signal 120 and separates the modulated power signal 120 into the stimulation signal and the power signal. The implanted unit 104 generates a stimulus based on the stimulation signal and delivers the stimulus to a body part in an auditory pathway of the recipient. In the example of FIG. 1, in which the hearing prosthesis 100 is a partially implantable cochlear implant, the implanted unit 104 includes an electrode array 106 that is implanted in one of the recipient's cochleae. Upon receiving the stimulation signal, the implanted unit 104 generates an electrical signal based on the stimulation signal. The implanted unit 104 sends the electrical signal to the electrode array 106, which causes one or more electrodes included on the electrode array 106 to deliver one or more electrical stimuli to the recipient's cochlea. Stimulating the recipient's cochlea causes the recipient to perceive at least a portion of the sound 110.

In an example in which the hearing prosthesis 100 is not a cochlear implant, the implanted unit 104 includes a component that is implanted (or otherwise placed) in one of the recipient's auditory nerves, the recipient's brain, or any other body part capable of being stimulated to assist the recipient in perceiving at least a portion of a sound. Delivering a stimulus to the body part stimulates the body part, allowing the recipient to perceive at least a portion of the sound 110.

2. Example Components of the Hearing Prosthesis

Figure 2:
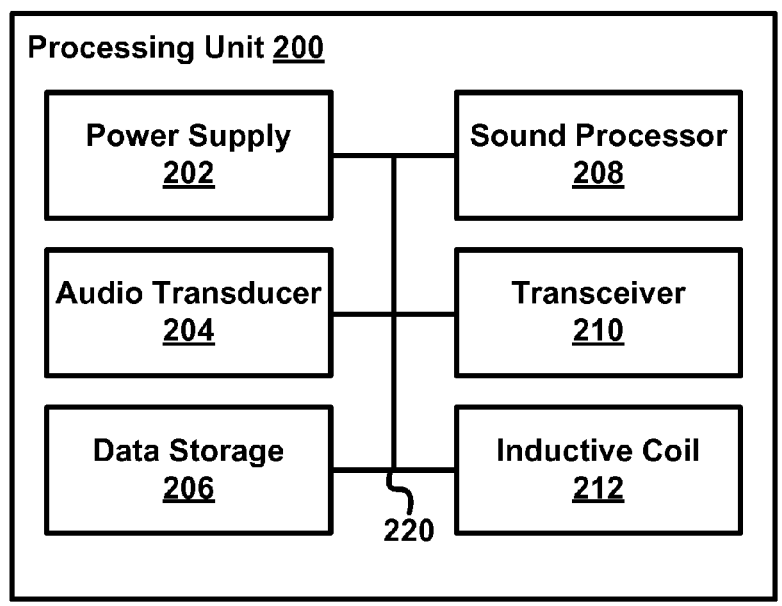
FIG. 2 is a block diagram of components of a processing unit depicted in FIG. 1, according to an example.

FIG. 2 is a block diagram of a processing unit 200. The processing unit 200 is one example of the processing unit 102 depicted in FIG. 1. The processing unit 200 includes a power supply 202, an audio transducer 204, a data storage 206, a sound processor 208, a transceiver 210, and an inductive coil 212, all of which may be connected directly or indirectly via circuitry 220. For illustrative purposes, the processing unit 200 is the processing unit 102 depicted in FIG. 1.

The power supply 202 supplies power to various components of the processing unit 200 and can be any suitable power supply, such as a rechargeable or a non-rechargeable battery. The power supply 202 also provides power to the implanted unit 104 via the inductive coil 212. In one example, the power supply 202 is a battery that can be charged wirelessly, such as through inductive charging. In another example, the power supply 202 is not a replaceable or rechargeable battery and is configured to provide power to the components of the processing unit 200 for the operational lifespan of the processing unit 200 and the implanted unit 104.

The audio transducer 204 receives the sound 110 from a source in an environment and sends a sound signal to the sound processor 208 that includes information indicative of the sound 110. In one example, the processing unit 200 is a cochlear implant. In another example, the processing unit 200 is an auditory brain stem implant or any other hearing prosthesis or combination of hearing prostheses now known (e.g., a hearing prosthesis system combining electrical and mechanical stimulation) or later developed that is suitable for assisting a recipient of the hearing 100 in the perceiving sound 110. In this example, the audio transducer 204 is an omnidirectional microphone, a directional microphone, an electro-mechanical transducer, or any other audio transducer now known or later developed suitable for use in the type of hearing prosthesis employed. Furthermore, in other examples the audio transducer 204 includes one or more additional audio transducers.

The data storage 206 includes any type of non-transitory, tangible, computer-readable media now known or later developed configurable to store program code for execution by a component of the processing unit 200 and/or other data associated with the processing unit 200. The data storage 206 stores information used by the sound processor 208 to process the sound signal. The data storage 206 may also store one or more computer programs executable by the sound processor 208.

The sound processor 208 is configured to determine a stimulation signal suitable for causing the implanted unit 104 to deliver a stimulus to a body part in one of the recipient's auditory pathways. In one example, the sound processor 208 includes one or more digital signal processors. In another example, the sound processor 208 is any processor or combination of processors now known or later developed suitable for use in a hearing prosthesis. Additionally, the sound processor 208 may include additional hardware for processing the sound signal, such as an analog-to-digital converter and/or one or more filters.

The sound processor 208 determines the stimulation signal by processing the sound signal received from the audio transducer 204. The stimulation signal includes information indicative of a stimulus current for one or more of the electrodes included on the electrode array 106. In one example, the sound processor 208 processes the sound signal as described herein with respect to FIGS. 4A and 4B. Additionally, the sound processor 208 accesses the data storage 206 to retrieve one or more computer programs that cause the sound processor 208 to execute at least a portion of the methods described herein with respect to FIGS. 5 and 6.

The transceiver 210 receives the stimulation signal from the sound processor 208 and modulates the stimulation signal with the power signal to form the modulated power signal 120. In one example, the transceiver 210 modulates the stimulation signal with the power signal using a time-division multiple-access modulation scheme. In another example, the transceiver 210 uses any modulation scheme now known or later developed suitable for inductively transmitting the stimulation signal and the power signal to the implanted unit 104.

The transceiver 210 sends the modulated power signal to the inductive coil 212, which inductively transmits the modulated power signal 120 to the implanted unit 104. The inductive coil 212 is constructed of any material or combination of materials suitable for inductively transferring the modulated power signal 120 to the implanted unit 104.

Figure 3A:
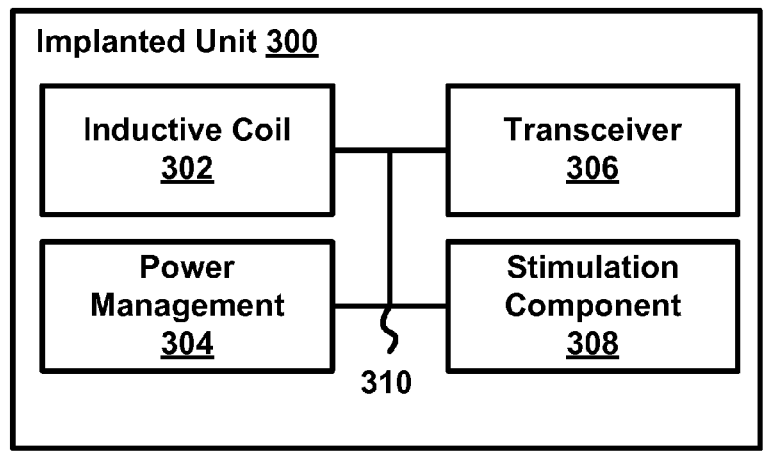
FIG. 3A is a block diagram of components of an implanted unit depicted in FIG. 1, according to an example.

FIG. 3A is a block diagram of an implanted unit 300 of a hearing prosthesis. The implanted unit 300 is one example of the implanted unit 104 depicted in FIG. 1. The implanted unit 300 includes an inductive coil 302, power management 304, a transceiver 306, and a stimulation component 308, all of which are connected directly or indirectly via circuitry 310. For illustrative purposes, the implanted unit 300 is the implanted unit 104 depicted in FIG. 1.

The inductive coil 302 inductively receives the modulated power signal 120 from the processing unit 102. The inductive coil 302 is constructed of any biocompatible material or combination of materials suitable for inductively receiving power from the processing unit 102. The inductive coil 302 transfers the power signal to the power management 304. The power management 304 distributes power to the components of the implanted unit 300. The power management 304 includes a component suitable for separating the modulated power signal 120 into the stimulation signal and the power signal, such as the component described with respect to FIG. 3B.

Figure 3B:
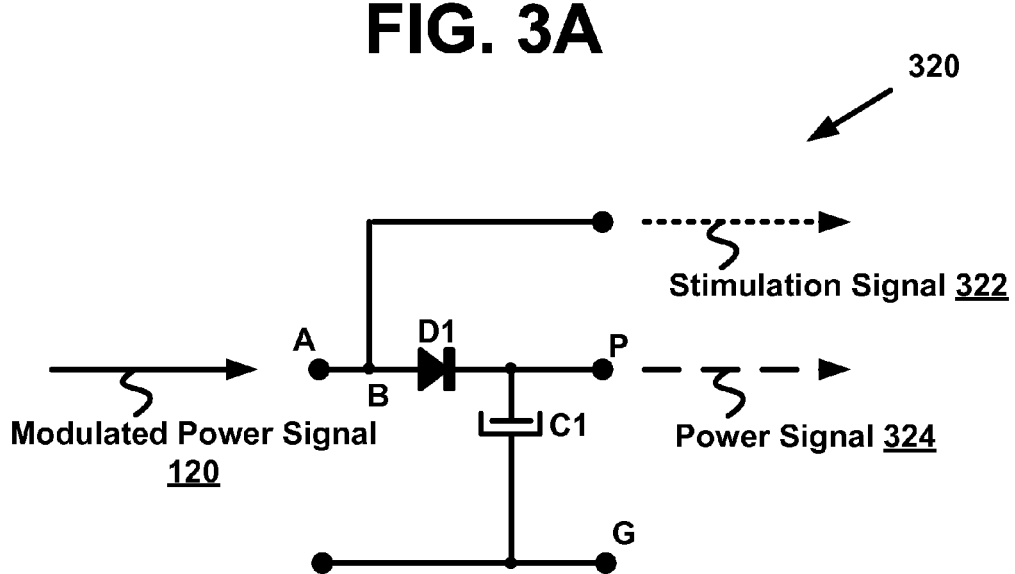
FIG. 3B is an electrical diagram of a component configured to separate a power signal and a data signal, according to an example.

FIG. 3B is an electrical diagram of a component 320 configured to separate the modulated power signal 120 into the stimulation signal and the power signal. The component 320 includes a rectifier formed by a diode D1 and a capacitor C1. Characteristics of the diode D1 and the capacitor C1 depend on the modulation frequency of the modulated power signal 120. The stimulation signal 322 is extracted from the modulated power signal 120 at a point B upstream of the diode D1. The rectifier removes the stimulation signal 322 from the modulated power signal 120, allowing the power signal 324 to be extracted at terminal P with respect to the reference ground G.

Returning to FIG. 3A, the power management 304 sends the stimulation signal to the transceiver 306, which transfers the stimulation signal to the stimulation component 308. The stimulation component 308 generates a stimulus based on the stimulation signal. In one example, the stimulation component 308 includes a first subcomponent configured to generate the stimulus and a second subcomponent configured to deliver the stimulus to a body part in an auditory pathway, such as a cochlea, an auditory nerve, a brain, and any other organ or body part capable of assisting a recipient in perceiving at least a portion of the sound 110. The first subcomponent generates the stimulus and sends the stimulus to the second component. The second subcomponent delivers the stimulus to the body part of the recipient.

For instance, since implanted unit 300 is the implanted unit 104, the stimulation component 308 includes a signal generator and the electrode array 106. The signal generator generates an electrical signal based on the stimulation signal and sends the electrical signal to the electrode array 106. The electrical signal causes one or more of the electrodes included on the electrode array 106 to deliver one or more electrical stimuli to a portion of the recipient's cochlea. The one or more electrical stimuli cause the cochlea to stimulate an auditory nerve, thereby allowing the recipient to perceive at least a portion of the sound 110.

3. Example System For Processing Sound Using A Masking Model

FIG. 4A is a block diagram of a system 400 for processing an audio signal. The system 400 includes an audio transducer 402, a pre-filter module 404, a filter bank module 406, a channel selection module 408, and a channel mapping module 410. For illustrative purposes, the system 400 is described with reference to the processing unit 200.

The audio transducer 402 is the same as or is substantially similar to the audio transducer 204. In one example, the sound processor 208 includes hardware and/or software configurable to perform the operations described with respect to the modules 404-410. In another example, the processing unit 200 includes one or more additional components configured to assist the sound processor 208 in performing the operations described with respect to the module 404-410. For instance, if the sound processor 208 performs the operations described with respect to modules 406-410, the processing unit 200 includes an additional component configured to perform the operations described with respect to the pre-filter module 404.

The audio transducer 402 receives a sound 412 from the environment. The audio transducer 402 sends an audio signal 414 that includes information indicative of the sound 412 to the pre-filter module 404. The pre-filter module 404 includes an amplifier configured to amplify high frequency components of the audio signal 414. The pre-filter module 404 is also configured to employ an adaptive gain control. The adaptive gain control accounts for variations in an amplitude of the audio signal 414. The pre-filter module 404 further includes an analog-to-digital converter suitable for digitizing the audio signal 404. In one example, the analog-to-digital converter uses a sampling rate of 16 KHz to generate a 16-bit digital signal. In another example, a different sampling rate and/or bit representation is used when digitizing the audio signal 414.

The output of the pre-filter module 404 is a digital signal 416. The filter bank module 406 receives the digital signal 416 and generates a spectral signal 418 that includes one or more spectral components of the digital signal 416. A spectral component of the digital signal 416 is a sound pressure level (SPL) corresponding to a frequency channel. In one example, frequency channels are linearly spaced below 1 KHz and logarithmically spaced above 1 KHz. In another example, the frequency channels are spaced according to any scheme suitable for processing the digital signal 416.

The filter bank module 406 determines M spectral components corresponding to M frequency channels, where M is an integer greater than one. For a cochlear implant, M may be equal to a number of electrodes included on an electrode array. That is, each of the M electrodes corresponds to a frequency channel. In one example, M is twenty-two. In another example, M is greater than or less than twenty-two, and may depend on a number of surviving neurons in the recipient's cochlea. For another type of hearing prosthesis, the value of M is any integer suitable for generating a stimulation signal.

The filter bank module 406 contains M pairs of band-pass filters and envelope detectors. Each pair of band-pass filters and envelope detectors corresponds to a frequency channel.

A portion of the digital signal 416 passes through each band-pass filter, and an associated envelope detector determines an envelope of the portion of the digital signal 416. In one example, each band-pass filter is implemented using a Fast Fourier Transform. The output of each envelope detector is based on an envelope of a portion of the digital signal 416 that passes through an associated band-pass filter. In one example, the output of each envelope detector is an SPL corresponding to a center frequency of the associated band-pass filter. In another example, the output of each envelope detector is a maximum SPL or an average SPL of the envelope. The filter bank module 406 generates the spectral signal 418 based on the outputs of the M envelope detectors.

The channel selection module 408 receives the spectral signal 418 and determines a channel-magnitude sequence 420. In one example, the channel selection module 408 employs a masking model to determine the channel-magnitude sequence 420. FIG. 4B is a block diagram of the channel selection module 408. The channel selection module 408 includes a band selection module 430, a masking model 432, and a buffer 434. The band selection module 430 is configured to select N spectral components to include in the channel-magnitude sequence 420, where N is an integer that is less than M.

For a cochlear implant, such as the hearing prosthesis 100 depicted in FIG. 1, the value of N depends on a desired frequency resolution of the recipient's perception of the sound 412 and a stimulation rate of each frequency channel. In general, the frequency resolution increases as N increases because more electrodes included on the electrode array 106 stimulate the recipient's cochlea. However, because the electrodes are stimulated sequentially, a channel stimulation rate decreases as N increases, thereby reducing a temporal resolution of the sound (i.e., a delay in the recipient perceiving the sound 412). Thus, N is selected to maximize the frequency resolution and the temporal resolution of the sound perceived by the recipient.

The band selection module 430 makes the selections by comparing the spectral signal 418 to a masking curve 440 based on the masking model 432. The masking model 432 is predicated on one or more "masking" effects caused by the physiology of the auditory pathway in humans (i.e. electrophysical masking) and/or processing of electrical stimuli by the human brain (i.e. psychoacoustic masking effect). At a basic level, the masking effects occur in the frequency domain ("simultaneous masking") and the time domain ("temporal masking). In the case of simultaneous masking, a tone of frequency $f_x$ and a magnitude $SPL_x$ prevents a simultaneous perception of tones with frequencies near $f_x$ and magnitudes sufficiently lower than $SPL_x$.

Temporal masking can be either "forward" masking or "backward" masking. In the case of forward masking, a first tone having a frequency $f_x$ and magnitude $SPL_x$ prevents a subsequent perception of a second tone having the frequency $f_x$ and a magnitude that is sufficiently less than $SPL_x$ within a given time interval. Backward masking refers to a scenario in which a second tone of frequency $f_x$ and magnitude $SPL_x$ prevents perception of a preceding first tone of frequency $f_x$ and a magnitude that is sufficiently less than $SPL_x$ within a given time interval. The masking model 432 models both simultaneous and temporal masking effects to reduce a number of spectral components of a sample of an audio signal needed to allow the recipient to perceive at least a portion of the sound.

The masking curve 440 includes M masking spectral components. The masking model 432 determines SPLs for the M masking spectral components based on spectral information from prior or subsequent sound samples to account for at least an effect due to temporal masking. The masking model 432 may also account for an effect due to simultaneous masking. The resulting initial masking curve (i.e., the masking curve 440 that is used to select a first spectral component of the spectral signal 418 to include in the stimulation signal) has variable masking spectral components. That is, an initial masking curve for a given sample may have one or more different masking spectral components than an initial masking curve for another sample.

Using the masking model 432 may lead to a different selection of frequency channels when determining the channel-magnitude sequence 420 as compared to using a standard initial masking curve. Employing the masking model 432 may thus enhance the frequency resolution of sounds perceived by the recipient, thereby allowing the recipient to more clearly perceive sounds having multiple spectral components, such as speech. The masking model 432 also promotes efficient use of the hearing prosthesis' power resources because the recipient is more likely to perceive the stimuli at the N selected frequency channels as compared to a recipient using a hearing prosthesis that does not employ the masking model 432.

The band selection module 430 sends a spectral set ($f_n$, $SPL_n$) to the buffer 434, where $f_n$ is a selected frequency channel and $SPL_n$ is a magnitude of the spectral component of the spectral signal 418 corresponding to the selected frequency channel $f_n$. In order to allow the band selection module 430 to select a next spectral set ($f_{n+1}$, $SPL_{n+1}$), the masking model 432 updates the masking curve 440 by increasing the masking spectral component corresponding to the previously selected frequency channel $f_n$. In one example, one or more additional spectral components corresponding to one or more additional frequency channels are also increased to model the masking effect of the selected spectral component.

By comparing the spectral signal 418 to the masking curve 440, the band selection module 430 selects the N spectral components that enhance the frequency resolution for a given value of N. The buffer 434 stores the spectral sets until the $N^{th}$ spectral set ($f_N$, $SPL_N$) is selected. The buffer 434 includes the N spectral sets in the channel-magnitude sequence 420. For instance, if N is five, then the channel-magnitude sequence 420 includes five spectral sets (i.e., ($f_1$, $SPL_1$), ($f_2$, $SPL_2$) . . . ($f_5$, $SPL_5$)). Methods for selecting a frequency channel and spectral component and updating the masking curve 440 are described herein with respect to FIGS. 5 and 6. In another example, the band selection module 430 includes a spectral set in the N spectral sets if the difference between the associated spectral component and the masking spectral component is above a threshold. Thus, in some situations, the number of spectral sets included in the channel-magnitude sequence is less than N.

In the preceding examples, the masking model 432 is based on improving a perceived quality of the sound 110 by the recipient. Alternatively, the masking model 432 improves a different operating characteristic of the hearing prosthesis, such as reducing the power consumption of the implanted unit and/or the processing unit 200. In one example, the masking model 432 adjusts the masking curve 440 based on another sample of the spectral signal 418 and employs a selection criterion for selecting the N spectral sets that does not depend on sound quality. For example, the band selection module 430 does not select a frequency channel that is adjacent to a previously selected frequency channel. Since a stimulus at a given selected frequency is likely to mask stimuli at frequencies adjacent to the given selected frequency, the band selection module 430 does not select at least the frequency channels adjacent to the previously selected frequency channel. For instance, if frequency channel 10 is a selected frequency channel, the band selection module 430 will not subsequently select frequency channel 9 or frequency channel 11. This is due to the likelihood that a stimulus at frequency channel 10 will mask stimuli at frequency channel 9 and frequency channel 11. The selection criterion may thus better allocate the power resources of the implanted unit 300, as the stimulation signal includes spectral components of the spectral signal 418 that the recipient is more likely to perceive. In other words, power is not wasted on generating stimuli that the recipient will not or is less likely to perceive. Additionally, the sound processor 208 may omit frequency channels adjacent to the given selected frequency when generating the spectral signal 418, thus reducing an amount of power consumed by the sound processor 208.

In yet another example, the band selection module 430 may omit a set of frequency channels from the M frequency channels when selecting the N spectral sets. In this example, the spectral signal 418 includes O frequency channels, where O is an integer less than M. The band selection module 430 selects the N spectral sets based on O differences between the spectral signal 418 and the masking curve 440. For instance, consider a situation in which the sound processor 208 determines that $k^{th}$ spectral signal has X peaks within a frequency range of about 100 Hz to about 500 Hz. The band selection module 430 may determine that a primary source of the sound 110 is a person speaking. The sound processor 208 subsequently omit R higher frequency channels from the M frequency, where R is an integer less than M and the sum of O and R is M. The band selection module 430 selects the N selected spectral components from O frequency channels. The band selection module 430 continues to omit the R frequency channels until the band selection module 430 determines that a $l^{th}$ spectral signal does not include X peaks within the frequency range of about 100 Hz to about 500 Hz.

Returning to FIG. 4A, the channel mapping module 410 receives the channel-magnitude sequence 420 and generates a pulse sequence 422. For each of the N selected spectral components, the channel mapping module 410 determines a pulse set $(f_n, I_n)$, where $I_n$ is a current for an electrode corresponding to the frequency channel $f_n$. Each electrode included on the electrode array 106 has a mapping curve that indicates a stimulus current for the electrode as a function of SPL. Fitting, or calibrating, the hearing prosthesis 100 to the recipient typically involves determining a threshold current (T-Level) and a maximum comfort level (C-Level) for each electrode. The T-Level is a stimulus current below which the recipient is unable to perceive a tone at a given frequency corresponding to the electrode. The C-Level is a stimulus current above which the recipient perceives the tone as being too loud. In one example, the current is zero if the SPL is less than a threshold level ($SPL_T$), the current varies approximately logarithmically between the T-Level and the C-Level if the SPL is between $SPL_T$ and a maximum level ($SPL_C$), and the current is the C-Level if the SPL is greater than an $SPL_C$. For each electrode, the channel mapping module 410 identifies the current corresponding to the SPL on the electrode's mapping curve.

In one example, the channel-mapping module 410 may arrange one or more pulse sets from high frequency to low frequency if N is greater than one. For example, if N is three, the pulse sequence 422 includes three pulse sets: $(f_1, I_1)$, $(f_2, I_2)$, and $(f_3, I_3)$. If $f_3$ is greater than $f_2$ and $f_2$ is greater than $f_1$, the channel mapping module 410 arranges the pulse sets in the pulse sequence 422 in the following order: $(f_3, I_3)$, $(f_2, I_2)$, $(f_1, I_1)$. The sound processor 208 then uses the pulse sequence 422 to generate the stimulation signal that is sent to the implanted unit 104.

4. Example Methods For Sound Processing Using A Masking Model

Figure 5:
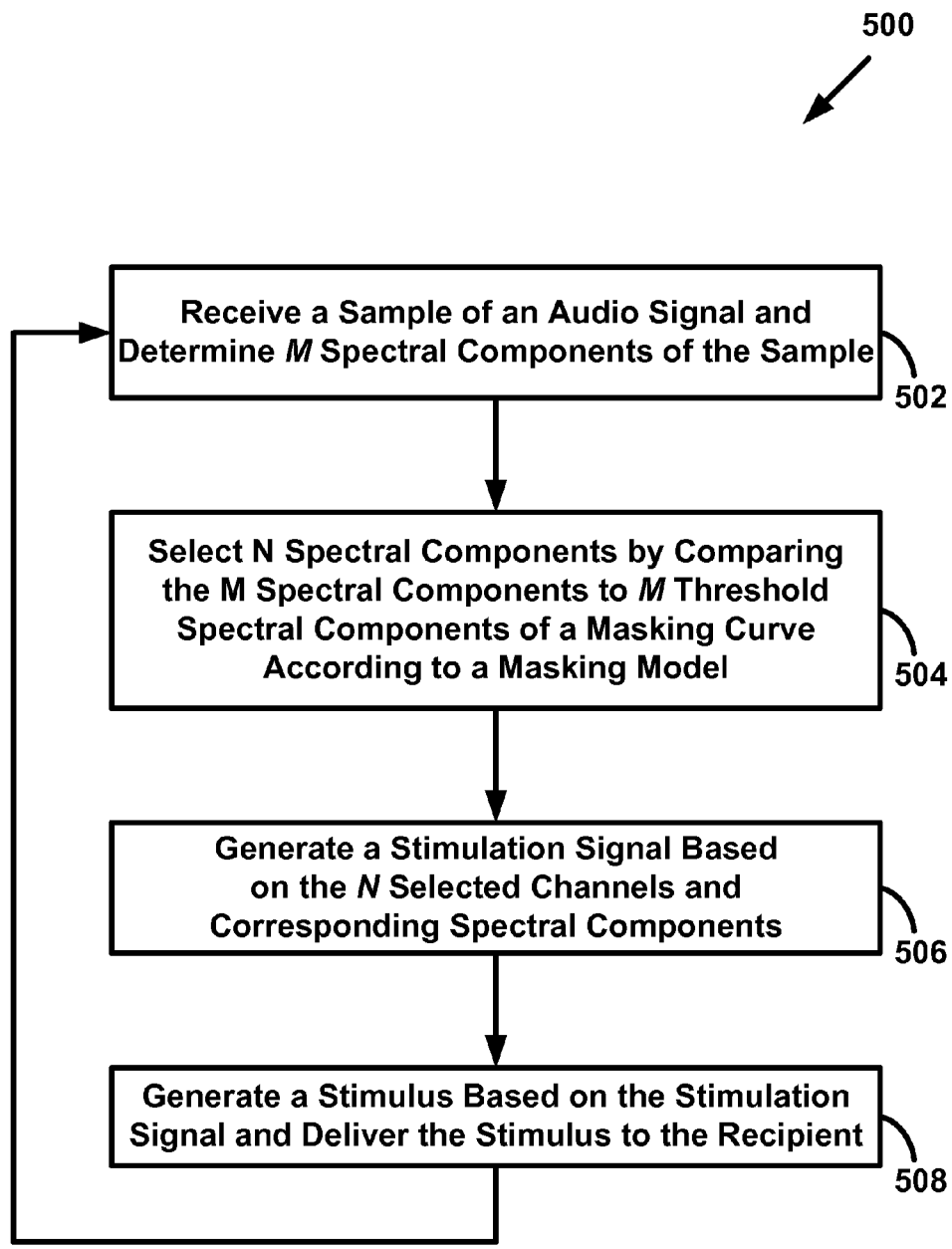
FIG. 5 is a flow diagram of a method for processing a sound according to a masking model of human hearing, according to an example.

FIG. 5 is a flow diagram of a method 500 for processing a sound using a masking model. A sound processor performs the steps of one or more blocks of the method 500 to determine a channel mapping sequence for a digital sample of an audio signal. While the processing unit 200 and the implanted unit 300 are described for purposes of illustrating the method 500, it is understood that other devices may be used.

At block 502, the method 500 includes receiving a sample of an audio signal and determining spectral components of the sample. In one example, the sound processor 208 determines the spectral components of the audio signal by implementing the functions described with respect to the modules 404-406 of FIG. 4A. In another example, the sound processor 208 uses any process or combination of processes suitable for determining the spectral components of a sample of the audio signal.

At block 504, the method 500 includes selecting N channels to include in a stimulation signal by comparing the spectral components of the sample to spectral components of a masking curve based on a masking model. The masking model accounts for at least an effect due to temporal masking. In one example, the masking model also accounts for an effect due to simultaneous masking. For instance, the masking model accounts for one or more effects due to simultaneous masking and forward masking. As another example, the masking model accounts for one or more effects due to simultaneous masking and backward masking. A method for selecting the N channels to include in the stimulation signal is described herein with respect to FIG. 6.

At block 506, the method 500 includes generating a stimulation signal based on the N selected channels and corresponding spectral components. As discussed with respect to FIG. 4B, the sound processor 208 determines the channel-magnitude sequence 420 when performing the functions of the channel selection module 408. The sound processor 208 performs the functions of the channel mapping module to determine the pulse sequence 422. The sound processor includes the pulse sequence 422 in the stimulation signal and sends the stimulation signal to the transceiver 210 for transmission to the implanted unit 300.

At block 508, the method 500 includes generating a stimulus based on the stimulation signal and delivering the stimulus to the recipient. The transceiver 210 generates the modulated power signal by modulating the stimulation signal with the power signal received from the power supply 202. The transceiver 210 sends the modulated power signal to the induction coil 212, which inductively transfers the modulated power signal to the induction coil 302 of the implanted unit 300. The power management 304 separates the components of the modulated power signal and sends the stimulation signal to the transceiver 306. The stimulation decoder 306 decodes the stimulation signal and sends the decoded stimulation signal to the stimulation component 308. The stimulation component 308 generates the stimulus based on the stimulation signal and delivers the stimulus to the recipient.

Once the steps of block 508 are performed, one iteration of the method 500 is complete. The method 500 includes returning to block 502 to perform a next iteration of the method 500, in which a next sample k+1 is received at block 502. The sound processor 208 continues performing iterations of the method 500 until the processing unit 200 is placed in a condition in which sound processing is not required, such as when the recipient removes the processing unit 200 in order to charge a battery of the power supply 202.

Figure 6:
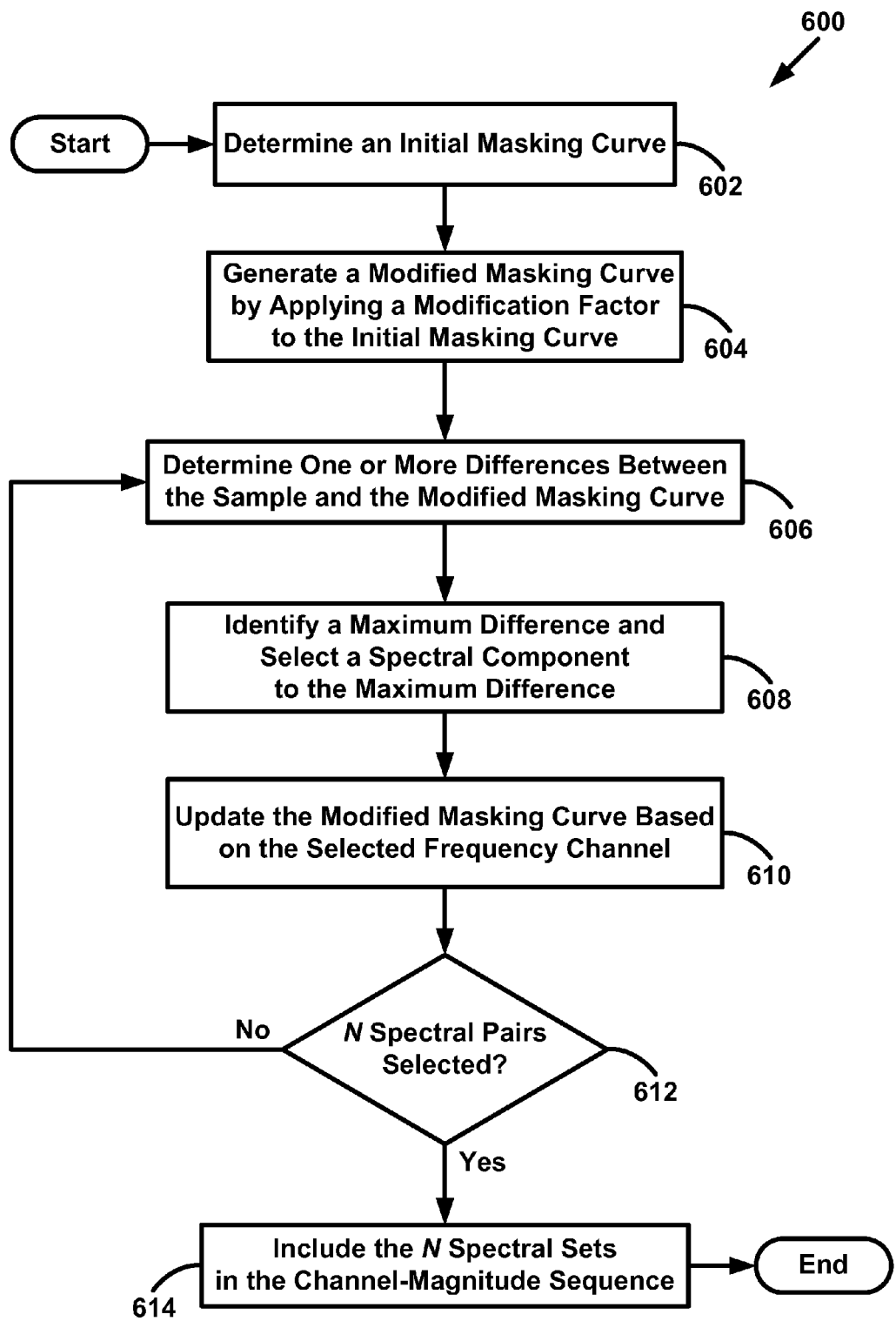
FIG. 6 is a flow diagram of a method for selecting one or more frequency channels according to a masking model of human hearing, according to an example.

FIG. 6 is a flow diagram of a method 600 for selecting one or more frequency channels using a masking model. The method 600 is one example of a method that a sound processor may employ when performing the steps of block 504 of the method 500. While the processing unit 200 and the channel selection module 408 are described for purposes of illustrating the method 600, it is understood that other devices may be used.

At block 602, the method 600 includes determining an initial masking curve. The masking model 432 accounts for at least a temporal masking effect. In one example, the temporal masking effect is due to forward masking. In this example, the initial masking curve is a masking curve used in processing a prior sample of an audio signal. For instance, the initial masking curve for the $k^{th}$ sample is a masking curve corresponding to the $k-1^{th}$ sample. Alternatively, the sound processor 208 determines the initial masking curve for the $k^{th}$ sample based on one or more spectral components of the channel-magnitude sequence 420 for the $k-1^{th}$ sample.

In another example, the masking model 432 is based on backward masking. Here, the initial masking curve is based on one or more spectral components of a next sample. That is, the initial masking curve for the $k^{th}$ sample is based on one or more spectral components of the $k+1^{th}$ sample. Additionally, in either of the prior to examples, the initial masking curve may account for an effect due to simultaneous masking.

In still another example, the initial masking curve is based on a threshold-in-quiet curve. The threshold-in-quiet curve represents the minimal magnitude SPL that a person having normal hearing can hear in a corresponding frequency channel. The sound processor 208 may use the threshold-in-quiet curve when there is not a prior sample on which to base the masking curve, such as when the sound processor 208 processes a first sample of the audio signal. In a further example, the initial masking curve is based on a different set of baseline spectral components corresponding to the M frequency channels that is suitable for initializing the masking curve.

In one example, the data storage 206 stores the initial masking curve, and the sound processor 208 accesses the data storage 206 to determine the initial masking curve. Alternatively, the data storage 206 stores information indicative of the initial masking curve, such as the one or more spectral components of the $k-1^{th}$ channel-mapping sequence, the one or more spectral components of the $k-1^{th}$ sample, or the one or more spectral components of the $k+1^{th}$ sample. The sound processor 208 accesses the data storage 206 to retrieve the information indicative of the initial masking curve, and the sound processor 208 determines the initial masking curve according to the masking model 432.

At block 604, the method 600 includes generating a modified masking curve by applying a modification factor to the initial masking curve. The sound processor 208 modifies the initial mapping curve for the $k^{th}$ sample to obtain a desired frequency resolution. In one example, such as when the masking model 432 accounts for simultaneous and forward masking, the modification factor is an attenuation factor, such as a factor of 0.2 or 0.5. In another example, such as when the masking model 432 accounts for temporal masking only, the modification factor is greater than zero.

The sound processor 208 generates the modified masking curve by applying the modification factor to each of the one or more spectral components of the initial masking curve. The data storage 206 stores the modification factor, and the sound processor 208 identifies the modification factor by accessing the data storage 206. In one example, the sound processor 208 applies the same modification factor to each of the one or more spectral components of the $k^{th}$ sample. In another example, the modification factor for a spectral component depends on a corresponding frequency channel. For instance, the sound processor 208 applies a first modification factor to spectral components corresponding to a first set of frequency channels and a second modification factor to a second set of frequency channels.

At block 606, the method 600 includes determining one or more differences between the sample and the modified masking curve. For each frequency channel, the sound processor 208 determines a difference between a spectral component of the sample and a masking spectral component of the modified masking curve. In one example, the sound processor 208 stores the one or more differences in the data storage 206, perhaps in an M×2 matrix.

In another example, the sound processor 208 compares a first difference to a second difference and stores the greater of the two differences, and corresponding frequency channel, in the data storage 206. For instance, the sound processor 208 determines a first difference for a first frequency channel and a second difference for a second frequency channel. The sound processor 208 compares the first difference to the second difference, and determines that the first difference is greater than the second difference. The sound processor 208 stores the first difference in the data storage 206. The sound processor 208 then determines a third difference for a third frequency channel and compares the third difference to the first difference. If the third difference is greater than the first difference, the sound processor 208 replaces the first difference in the data storage 206 with the third difference. If the first difference is greater than the third difference, the sound processor 208 maintains the first difference in the data storage 208. The sound processor 208 repeats this process until a difference is determined for each of the M frequency channels.

At block 608, the method 600 includes identifying a maximum difference and selecting a spectral pair corresponding to the maximum difference. The sound processor 208 identifies the maximum difference by accessing the data storage 206. The sound processor 208 then selects the spectral pair ($f_n$, $SPL_n$) corresponding to the maximum difference for inclusion in the channel-magnitude sequence 420. For instance, if the maximum difference corresponds to a seventh frequency channel $f_7$, the sound processor selects the spectral pair ($f_7$, $SPL_7$) for inclusion in the channel-magnitude sequence. The sound processor 208 stores the spectral pair in the buffer 434.

At block 610, the method 600 includes updating the modified masking curve based on the selected frequency channel. The sound processor 208 updates the modified masking curve according to the masking model 432. In one example, the masking model 432 accounts for simultaneous masking. In this example, the sound processor 208 superposes a spreading function on the modified masking curve. The spreading function models the effect of frequency masking by increasing the masking spectral components corresponding to the selected frequency channel $f_n$ and one or more frequency channels adjacent to the selected frequency channel $f_n$. The spreading function is centered at the selected frequency channel $f_n$ and has a maximum value at the selected frequency channel $f_n$. The value of the spreading function decreases approximately linearly in the linear domain within a range from the selected frequency channel.

Modifying the masking curve in this manner reduces a likelihood that a spectral component corresponding to a frequency within a range of the selected frequency channel $f_n$ is selected as one of the N spectral components for the $k^{th}$ sample. For instance, if $f_n$ is an eleventh frequency channel $f_{11}$ of twenty-two possible frequency channels, applying the spreading function at the eleventh frequency channel may reduce the differences between the spectral components of the signal and the masking spectral components corresponding to a ninth frequency channel $f_9$, tenth frequency channel $f_{10}$, the twelfth frequency channel $f_{12}$, and/or thirteenth frequency channel $f_{13}$.

Modifying the masking curve in this manner also reduces a likelihood that a spectral component corresponding to the selected frequency channel $f_n$ or adjacent to the selected frequency channel $f_n$ is selected as one of the N spectral components for a later sample of the spectral signal. For instance, if one of the N selected frequency channels is the eleventh frequency channel $f_{11}$, centering the spreading function at $f_{11}$ makes it less likely that the tenth through twelfth frequency channels $f_{10}$-$f_{12}$ are selected as one of the N spectral components for the k+1 sample. The sound processor 208 updates the modified masking curve stored in the data storage 206 based on the update.

In another example, the masking model 432 does not account for simultaneous masking. The sound processor 208 applies an offset to the masking spectral component corresponding to the selected frequency channel $f_n$. Modifying the masking curve in this manner reduces a likelihood that a spectral component corresponding to the selected frequency channel $f_n$ is selected as one of the N spectral components in a later portion of the spectral signal. For instance, if the eleventh frequency channel $f_{11}$ is one of the N selected frequency channels for the $k^{th}$ sample, applying the offset makes it less like that the eleventh frequency channel $f_{11}$ is one of the N selected frequency channels for the k+1$^{th}$ sample. The sound processor 208 updates the modified masking curve stored in the data storage 206 based on the update.

At block 612, the method 600 includes determining whether N spectral pairs are selected. If the sound processor 208 has not selected N spectral pairs, the method 600 includes returning to block 606 to determine one or more additional differences between the sample and the modified masking curve. The one or more additional difference determined may vary from the one or more difference determined during the first performance of the steps of block 606 because of the update applied to the modified masking curve. The sound processor 208 continues performing the steps of blocks 606-610 until the sound processor 208 selects N spectral pairs. In one example, the sound processor 208 does not select a frequency channel adjacent to a previously selected frequency channel during subsequent iterations of the steps of block 606-610, regardless of the differences determined at block 606.

At block 614, the sound processor 208 includes the N spectral sets in the channel-magnitude sequence, which is used for determining the pulse sequence and the stimulation signal. In one example, the sound processor 208 stores the channel-magnitude sequence in the data storage 206. After completing the steps of block 614, the method 600 ends.

5. Conclusion

With respect to any or all of the message flow diagrams, scenarios, and flow charts in the figures and as discussed herein, each step, block and/or communication may represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages may be executed out of order from that shown or discussed, including in substantially concurrent or in reverse order, depending on the functionality involved. Further, more or fewer steps, blocks and/or functions may be used with any of the message flow diagrams, scenarios, and flow charts discussed herein, and these message flow diagrams, scenarios, and flow charts may be combined with one another, in part or in whole.

A step or block that represents a processing of information may correspond to circuitry that can be configured to perform the specific logical functions of a herein-described method or technique. Alternatively or additionally, a step or block that represents a processing of information may correspond to a module, a segment, or a portion of program code (including related data). The program code may include one or more instructions executable by a processor for implementing specific logical functions or actions in the method or technique. The program code and/or related data may be stored on any type of computer-readable medium, such as a storage device, including a disk drive, a hard drive, or other storage media.

The computer-readable medium may also include non-transitory computer-readable media such as computer-readable media that stores data for short periods of time like register memory, processor cache, and/or random access memory (RAM). The computer-readable media may also include non-transitory computer-readable media that stores program code and/or data for longer periods of time, such as secondary or persistent long term storage, like read only memory (ROM), optical or magnetic disks, and/or compact-disc read only memory (CD-ROM), for example. The computer-readable media may also be any other volatile or non-volatile storage systems. A computer-readable medium may be considered a computer-readable storage medium, for example, or a tangible storage device.

Moreover, a step or block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. A method comprising:
receiving a signal that includes information indicative of one or more spectral components of a sound;
determining a masking curve that includes information indicative of one or more masking spectral compo- nents, wherein the masking curve is determined according to a masking model of human hearing that accounts for at least an effect due to temporal masking; and generating a stimulus based on a difference between the signal and the masking curve, wherein the stimulus allows a recipient to perceive at least a portion of the sound.

2. The method of claim 1, wherein the masking model further accounts for an effect due to simultaneous masking.

3. The method of claim 1, wherein the effect due to temporal masking is an effect due to forward masking.

4. The method of claim 1, wherein:

the one or more spectral components of the signal include one or more input sound pressure levels corresponding to one or more frequency channels; and the one or more masking spectral components of the masking curve include one or more masking sound pressure levels corresponding to the one or more frequency channels.

5. The method of claim 4, wherein generating the stimulus includes:

identifying a stimulus frequency channel from the one or more frequency channels at which a difference between the signal and the masking curve is greatest, wherein the stimulus includes a spectral component of the signal corresponding to the stimulus frequency channel.

6. The method of claim 5, wherein generating the stimulus further includes:

determining a modified masking curve by increasing a value of a masking sound pressure level corresponding to the stimulus frequency channel; and identifying a second stimulus frequency channel from the one or more frequency channels at which a difference between the signal and the modified masking curve is greatest, wherein the stimulus includes a second spectral component of the signal corresponding to the second stimulus frequency channel.

7. The method of claim 5, wherein generating the stimulus further includes:

determining a modified masking curve by increasing values of masking sound pressure levels corresponding to the stimulus frequency channel and at least one frequency channel adjacent to the stimulus frequency channel; and identifying a second stimulus frequency channel from the plurality of frequency channels at which a difference between the signal and the modified masking curve is greatest, wherein the stimulus includes a second spectral component of the signal corresponding to the second stimulus frequency channel.

8. A method comprising:

determining M spectral components of a sample of an audio signal, wherein M is an integer greater than one;

selecting N spectral components to include in a stimulation signal from the M spectral components, wherein N is an integer greater than zero and less than M, and wherein the N spectral components depend on at least N previously selected spectral components; and generating the stimulation signal based on the N spectral components, wherein the stimulation signal includes information indicative of a stimulus that allows a recipient to perceive at least a portion of the audio signal, wherein selecting the N spectral components comprises:

determining that the N previously selected spectral components are indicative of speech;

identifying a one or more frequency channels having a frequency greater than a cut-off frequency; and determining that one or more spectral components corresponding to the one or more frequency channels are not one of the N spectral components.

9. The method of claim 8, wherein selecting the N spectral components comprises:

determining M masking spectral components, wherein the M masking spectral components are based on M prior masking spectral components used to select the N previously selected spectral components, and wherein the M masking spectral components account for at least an effect due to temporal masking;

determining a difference between the M spectral components and the M masking spectral components at each of M frequency channels; and identifying a stimulus frequency channel at which the difference between one of the M spectral components and one of the M masking spectral components is greatest, wherein a spectral component corresponding to the stimulus frequency channel is one of the N spectral components.

10. The method of claim 9, wherein determining the M masking spectral components comprises applying a modification factor to the M prior masking spectral components.

11. The method of claim 9, wherein determining the M masking spectral components comprises:

applying a first modification factor to a first set of prior masking spectral components; and applying a second modification factor to a second set of prior masking spectral components.

12. The method of claim 9, further comprising:

applying a spreading function centered at the stimulus frequency channel corresponding, wherein the spreading function increases a value of at least the masking spectral component corresponding to the stimulus frequency channel;

determining, for each of the M frequency channels, an additional difference between the spectral component and the masking spectral component; and identifying an additional stimulus frequency channel at which the additional difference between the spectral component and the masking spectral component is greatest, wherein a spectral component corresponding to the additional stimulus frequency channel is one of the N spectral components.

13. A method, comprising:

determining M spectral components of a sample of an audio signal, wherein M is an integer greater than one;

selecting N spectral components to include in a stimulation signal from the M spectral components, wherein N is an integer greater than zero and less than M, and wherein the N spectral components depend on at least N previously selected spectral components; and generating the stimulation signal based on the N spectral components, wherein the stimulation signal includes information indicative of a stimulus that allows a recipient to) perceive at least a portion of the audio signal, wherein selecting the N spectral components comprises:

identifying N prior frequency channels corresponding to the N previously selected spectral components;

identifying at least one masked frequency channel that is adjacent to each of the N prior frequency channels; and determining that a spectral component corresponding to one of the at least one masked frequency channels is not one of the N spectral components.

14. A non-transitory computer-readable memory having stored therein instructions executable by a computing device to cause the computing device to perform functions comprising:

determining an initial masking curve that includes one or more masking spectral components, wherein the initial masking curve is based on a masking model of human hearing that accounts for at least a temporal masking effect;

generating a modified masking curve by applying a modification factor to the initial masking curve, wherein the modified masking curve includes one or more modified masking spectral components;

determining one or more differences between one or more spectral components of an audio sample and the one or more modified masking spectral components, wherein the audio sample includes information indicative of a sound;

identifying a maximum difference from the one or more differences;

selecting a selected spectral component corresponding to the maximum difference; and generating a stimulus based on at least the selected spectral component, wherein the stimulus causes a recipient to perceive at least a portion of the sound.

15. The non-transitory computer-readable memory of claim 14, wherein the masking model accounts for simultaneous masking.

16. The non-transitory computer-readable memory of claim 14, wherein the initial masking curve is a masking curve used to generate a preceding stimulus, wherein the preceding stimulus and the stimulus are successive stimuli.

17. The non-transitory computer-readable memory of claim 14, wherein the modification factor is an attenuation factor.

18. The non-transitory computer-readable memory of claim 17, wherein the attenuation factor is one of about 0.2 or about 0.5.

19. The non-transitory computer-readable memory of claim 14, wherein the functions further comprise:

superposing a spreading function on the modified masking curve at a selected frequency channel corresponding to the selected spectral component, wherein the spreading function is centered at the selected frequency channel and increases a value of at least one masking spectral component;

determining one or more additional differences between the one or more spectral components of the sample and the one or more modified masking spectral components;

identifying a second maximum difference from the one or more additional differences;

selecting a second selected spectral component corresponding to the second maximum difference, wherein the stimulus is further based at least on the second selected spectral component.

20. The non-transitory computer-readable memory of claim 14, wherein determining the initial masking curve includes:

identifying a preceding stimulus, wherein the preceding stimulus and the stimulus are successive stimuli; and determining the initial masking curve based on one or more spectral components of the preceding stimulus.

21. The non-transitory computer-readable memory of claim 14, wherein the temporal masking effect is due to forward masking.

22. The non-transitory computer-readable memory of claim 14, wherein the modification factor is greater than zero.

23. The non-transitory computer-readable memory of claim 14, wherein the modification factor has a first value for a first set of frequency channels and a second value for a second set of frequency channels.

24. A sound processor configured to:

determine a digital sample of an audio signal;

determine one or more spectral components of the digital sample;

select one or more of the spectral components to include in a stimulation signal, wherein the one or more of the spectral components selected depends on at least one or more prior spectral components included in a prior stimulation signal;

generate the stimulation signal, wherein the stimulation signal includes information indicative of a stimulus that allows a recipient to perceive at least a portion of the audio signal, identify a masking frequency channel corresponding to one of the one or more prior spectral components; and determine at least one masked frequency channel that is adjacent to the masking frequency channel, wherein, to determine the one or more spectral components of the digital sample, the sound processor is further configured to determine that the digital sample does not include a spectral component at the at least one masked frequency channel.

25. The sound processor of claim 24, wherein, to select the one or more spectral components to include in the stimulation signal, the sound processor is further configured to:

generate a masking curve based on the one or more prior spectral components, wherein the masking curve includes one or more masking spectral components;

modify the masking curve by applying a modification factor;

determine one or more difference between the digital sample and the masking curve; and identify one or more selected frequency channels at which the difference is greatest, wherein one or more spectral components corresponding to the one or more selected frequency channels are included in the stimulation signal.

26. The sound processor of claim 25, wherein the modification factor is greater than zero and less than one.

27. The sound processor of claim 25, wherein the masking curve is based on a masking model that accounts for at least an effect due to temporal masking.

28. The sound processor of claim 24, wherein, to determine the one or more spectral components of the digital sample, the sound processor is further configured to:

identify M possible spectral components of the digital sample, wherein M is an integer greater than one; and select O spectral components from M possible spectral components, wherein the O spectral components are designated as the one or more spectral component of digital sample.

\* \* \* \* \*